United States Patent
Saur et al.

(10) Patent No.: US 12,236,613 B2
(45) Date of Patent: Feb. 25, 2025

(54) METHOD AND DEVICE FOR GENERATING A CONTROL SIGNAL, MARKER ARRAY AND CONTROLLABLE SYSTEM

(71) Applicants: Carl Zeiss Industrielle Messtechnik GmbH, Oberkochen (DE); Carl Zeiss Meditec AG, Jena (DE)

(72) Inventors: Stefan Saur, Aalen (DE); Zuzanna Derda, Katowice (PL); Stefan Schute, Aalen (DE); Adrian Samp, Slupsk (PL)

(73) Assignees: Carl Zeiss Industrielle Messtechnik GmbH, Oberkochen (DE); Carl Zeiss Meditec AG, Jena (DE)

( * ) Notice: Subject to any disclaimer, the term of this patent is extended or adjusted under 35 U.S.C. 154(b) by 1213 days.

(21) Appl. No.: 16/945,862

(22) Filed: Aug. 1, 2020

(65) Prior Publication Data
US 2020/0363782 A1   Nov. 19, 2020

Related U.S. Application Data

(63) Continuation of application No. PCT/EP2019/052469, filed on Feb. 1, 2019.

(30) Foreign Application Priority Data

Feb. 2, 2018 (DE) ............ 10 2018 201 612.7

(51) Int. Cl.
*G06T 7/246* (2017.01)
*A61B 90/00* (2016.01)
(Continued)

(52) U.S. Cl.
CPC .............. *G06T 7/246* (2017.01); *A61B 90/39* (2016.02); *G06T 1/0014* (2013.01); *G06T 7/73* (2017.01);
(Continued)

(58) Field of Classification Search
CPC ......... G06T 7/246; G06T 1/00; G06T 1/0014; G06T 7/73; G06T 2207/10012;
(Continued)

(56) References Cited

U.S. PATENT DOCUMENTS

| | | | |
|---|---|---|---|
| 7,668,584 B2 | 2/2010 | Jansen | |
| 8,172,775 B2 * | 5/2012 | Warkentine | ............ A61B 34/10 |
| | | | 600/595 |

(Continued)

FOREIGN PATENT DOCUMENTS

| | | |
|---|---|---|
| DE | 102015217314 A1 | 3/2016 |
| EP | 1872735 A1 | 1/2008 |

(Continued)

OTHER PUBLICATIONS

International Search Report and Written Opinion dated Apr. 15, 2019 of the international application PCT/EP2019/052469 on which this application is based and English language translation thereof.
(Continued)

*Primary Examiner* — Edward F Urban
*Assistant Examiner* — Benedict E Lee
(74) *Attorney, Agent, or Firm* — Ewers IP Law PLLC; Falk Ewers

(57) ABSTRACT

A method and a device for generating a control signal for a controllable device are provided. The controllable device has an optical position detection system. At least two images of at least one spatial region are generated with at least one optical detection device of the optical position detection system. Markers are identified in the images and the control signal is generated when a relative position between at least two markers changes. In addition, a marker array and a controllable system are provided.

16 Claims, 5 Drawing Sheets

(51) Int. Cl.
*G06T 1/00* (2006.01)
*G06T 7/73* (2017.01)
(52) U.S. Cl.
CPC ............ *A61B 2090/3937* (2016.02); *G06T 2207/10012* (2013.01)
(58) Field of Classification Search
CPC ......... A61B 17/00; A61B 90/00; A61B 90/39; A61B 2090/3937; A61B 90/20; A61B 2017/00207; A61B 2034/2055; A61B 2090/3983; A61B 34/20; G06F 3/0346; G06F 3/01; G06F 3/011; G06F 3/017; G06F 3/03; G06F 3/0308; G06F 3/0338; G06F 3/0362
See application file for complete search history.

(56) References Cited

U.S. PATENT DOCUMENTS

| | | | | |
|---|---|---|---|---|
| 9,274,187 | B2 * | 3/2016 | Griswold | ............... G06F 3/01 |
| 10,499,832 | B2 * | 12/2019 | Greene | ............... A61B 5/064 |
| 10,675,116 | B2 * | 6/2020 | Olive | ............... A61B 90/39 |
| 10,987,050 | B2 * | 4/2021 | Bonfils-Rasmussen | ............... A61B 1/00045 |
| 2005/0113659 | A1 | 5/2005 | Pothier et al. | |
| 2007/0016008 | A1 | 1/2007 | Schoenefeld | |
| 2007/0208252 | A1 * | 9/2007 | Makower | ............... A61B 6/032 606/198 |
| 2008/0021311 | A1 | 1/2008 | Goldbach | |
| 2010/0013764 | A1 | 1/2010 | Gu et al. | |
| 2015/0002540 | A1 | 1/2015 | De et al. | |
| 2016/0232713 | A1 * | 8/2016 | Lee | ............... G06F 3/011 |
| 2017/0168592 | A1 * | 6/2017 | Mishyn | ............... G06F 3/0325 |
| 2017/0172669 | A1 * | 6/2017 | Berkowitz | ............... A61B 90/96 |
| 2017/0258531 | A1 | 9/2017 | Bodjanski | |
| 2021/0038426 | A1 * | 2/2021 | Boularot | ............... A61B 18/203 |

FOREIGN PATENT DOCUMENTS

| | | |
|---|---|---|
| WO | 2009067726 A2 | 6/2009 |
| WO | 2012041371 A1 | 4/2012 |

OTHER PUBLICATIONS

Office Action issued in German Patent Application No. DE 10 2018 201 612.7, dated Oct. 4, 2018 (from which this application claims priority) and English language machine translation thereof.

* cited by examiner

METHOD AND DEVICE FOR GENERATING A CONTROL SIGNAL, MARKER ARRAY AND CONTROLLABLE SYSTEM

CROSS REFERENCE TO RELATED APPLICATIONS

This application is a continuation application of international patent application PCT/EP2019/052469, filed Feb. 1, 2019, designating the United States and claiming priority to German application 10 2018 201 612.7, filed Feb. 2, 2018, and the entire content of both applications is incorporated herein by reference.

TECHNICAL FIELD

The disclosure relates to a method and a system for generating a control signal with an optical position detection system. Furthermore, the disclosure relates to a marker array for generating such a control signal, and to a controllable system.

BACKGROUND

It is known to use optical position detection systems to determine a position and/or an orientation of an object in a reference coordinate system. Such optical position detection systems also make it possible to determine a movement, in particular a trajectory, of the object, that is to say a temporal sequence of positions and/or orientations.

Optical position detection systems are used in a plurality of fields of application. By way of example, optical position detection systems can be used in medical applications, for example in order to determine a position of medical, in particular surgical, instruments. Moreover, optical position detection systems can be employed in industrial applications for determining a position of movable parts of a machine or of a machine apparatus. In this regard, optical sensors or sensors that effect tactile measurement are used in industrial metrology, for example, wherein optical position detection systems can be used for determining a position of said sensors, in particular in measurement operation.

Over and above these two exemplary applications, however, use in a plurality of still further applications is possible.

It is known that markers or marker arrays can be used in order to be able to determine the position of an object reliably and accurately with an optical position detection system. For this purpose, said markers or marker arrays can be secured to the object to be tracked.

WO 2012/041371 A1 describes a method for controlling a device, in particular a medical device, which is controlled if predetermined criteria with regard to identified objects and persons and/or with regard to body parts are satisfied.

EP 1 872 735 A1 describes a method for identifying an instrument for navigation with a medical navigation system, wherein the instrument is provided with a reference array including a plurality of markers, the arrangement of which at the reference array forms a rigid body.

US 2017/258531 A1 describes an optical tracking system and tracking methods based on passive markers.

US 2007/0016008 A1 describes a surgical navigation system that uses selective gestures to generate input signals for a computer.

For this purpose, the markers can be secured for example to the object to be detected. Markers of this type can also be referred to as a target. In such a case, the markers can be imaged by a single image capture device or a plurality of image capture devices, wherein a position of the markers and thus also of the object to which the markers are secured can then be determined on the basis of the image data generated in this way. By way of example, a target with 3 markers and a single image capture device can be used for position determination. Methods for determining the position depending on or on the basis of image data generated in this way are known in this context to a person skilled in the art. In order to take account of a plurality of degrees of freedom, in particular six degrees of freedom, during the position determination, it may be necessary to secure a plurality of markers to the object. In this case, it is known that the spatial arrangement of a plurality of markers of a marker array relative to one another is invariable and can be previously known or calibratable. A marker array of this type may also be referred to hereinafter as a rigid marker array.

In applications in which optical position detection systems are used, in many cases there is also a desire for a user interaction for controlling a controllable system including the optical position detection system. By way of example, methods for touch-based interaction, for example the haptic operation of an input device, or interaction without touch, are known. Interaction without touch advantageously makes it possible that an activity carried out by the user need not be interrupted or an object currently held by the user need not be released in order to carry out the interaction.

In order to perform such an interaction without touch, a user can apply methods for voice control, for example, if said user does not wish to release an object held by said user.

It is desirable to provide simple and reliable generation of output signals for controlling a controllable system including an optical position detection system.

SUMMARY

The technical problem addressed is that of providing a method and a system for generating control signals for a controllable device with an optical position detection system, as well as a marker array and also a controllable system which enable faster, simplified and reliable generation of control signals.

The technical problem is resolved by a method for generating a control signal for a controllable device with an optical position detection system, a system for generating a control signal for activating a predetermined operating mode or deactivating the predetermined operating mode of a controllable device, and a controllable system as described herein.

The optical position detection system can include exactly one or at least one optical detection device, for example an image capture device, in particular a camera. The optical position detection system can be, e.g., a so-called stereoscopic image capture system having at least two image capture devices.

Images of a spatial region can be generated with the at least one optical detection device of the optical position detection system. Said spatial region can be referred to as the detection region of the optical position detection system.

Furthermore, with an evaluation device, it is possible to determine a position of at least one imaged object depending on the image data generated. For this purpose, it is possible to identify the at least one object in the image, for example with methods known to the person skilled in the art for object detection depending on image data. Furthermore, likewise with methods known to the person skilled in the art, it is possible to determine the position in a coordinate system of the optical position detection system. Said coordinate system of the optical position detection system can be registered to a reference coordinate system, that is to say that a coordinate transformation between the two coordinate systems is known. Methods of this type have been explained for example in US 2017/258531 A1, cited in the introduction. In this case, a position can denote a position and/or orientation.

The at least one optical detection device and the evaluation device can be connected in terms of signaling and/or data technology.

In this case, a controllable device can denote a device whose operation is controllable with a control signal. In particular, the controllable device can be a positioning device. The positioning device can serve in particular for positioning objects.

An object can be, e.g., an instrument, in particular a medical instrument. Moreover, an object can be a microscope or a part of the microscope. Moreover, an object can be a sensor, for example a sensor of a coordinate measuring machine that effects optical detection or tactile detection.

Such a positioning device can be embodied for example as a robot, in particular an articulated-arm robot. Alternatively, the positioning device can include linear drives, for example the linear drives of a coordinate measuring machine. Moreover, the controllable device can be the measuring machine explained above.

However, the disclosure is not restricted to these controllable devices presented by way of example. Rather, it is also possible for other devices that enable interaction with a user to be controlled with the control signal generated according to an aspect of the disclosure.

The control signal can be in particular an activation signal for activating or deactivating a predetermined operating mode of the controllable device. If the controllable device is a positioning device, for example, then the activation signal can serve for activating or deactivating a position tracking mode. In an activated position tracking mode, the positioning device can vary the position of an object to be positioned depending on, in particular proportional to, a change of the position of an instrument, for example of an instrument with a marker or a marker array, said change being carried out by the user.

Moreover, a control signal can be an activation signal for storing a current position of the instrument or the object to be positioned by the positioning device. In this case, said position can be stored, for example in a corresponding storage device.

In this regard, by way of example, a user can hold by hand a medical instrument, for example a surgical instrument. Furthermore, markers, in particular markers of a marker array, can be secured to the instrument, for example to a suction tube. If a position tracking module is then activated, a positioning device for a surgical microscope can be controlled in such a way that the surgical microscope keeps constant a relative position with respect to the instrument. In this case, the surgical microscope can follow the trajectory of the instrument. The surgical microscope can thus be repositioned without the need for manual actuation by a user. Alternatively, when generating the control signal, a current position of the surgical microscope or of the positionally tracked instrument can be stored. In this case, e.g., a position of the surgical microscope relative to the instrument and/or relative to a patient can be stored.

If the controllable system is a measuring device, then the control signal can be for example an activation signal for activating a measuring mode. If the measuring machine is a coordinate measuring machine, then in the activated measuring mode, with the sensor, coordinates can be detected and stored. Depending on these detected coordinates, e.g., an object size, an object shape or quality control of the object can then be carried out.

It goes without saying that other operating modes of the controllable device can also be activated or deactivated with the control signal, for example an illumination intensity variation mode or a camera zoom mode, a menu operation mode or an input mode.

In the operating modes activated in this way, control signals can then in turn likewise be generated depending on output signals of the optical position detection system or depending on further input signals, for example gesture recognition. In this regard, in the illumination intensity variation mode, e.g., an intensity of the illumination can be varied. In the camera zoom mode, a zoom of a camera can be varied. In the menu operation mode, menu subitems can be selected and optionally activated. In the input mode, a user input can be effected. The menu items or an input means can be generated virtually, for example by display on a display device or by projection onto a specific surface. In this regard, by way of example, a virtual keyboard can be displayed. Said menu items or input means can then be operated with the instrument held by the user. In an illumination change mode, e.g., switching on, switching off or variation of illumination scenarios can be effected.

In the method, at least two images of the spatial region are generated. The two images are generated temporally successively. Furthermore, markers, that is to say imaged markers, are identified in the images. The markers can be, in particular, markers of a marker array that is explained in even greater detail below. The marker array can be secured to an instrument or a sensor, wherein the instrument or the sensor can be activated by the user, for example by hand. Markers can be identified with methods for detecting image features that are known to the person skilled in the art. In this case, predetermined image-based properties, that is to say properties that are determinable from the image data, can be assigned to imaged markers. If such properties are detected in the image, then the corresponding marker can be identified. The markers can typically be so-called passive markers. It goes without saying, however, that it is also possible for the markers to be active markers.

According to an aspect of the disclosure, a control signal is generated if a relative position between at least two markers with respect to one another changes. The markers can typically be markers of a marker array. In this case, the relative position can change in a marker array-specific coordinate system. The latter can be different than a global reference coordinate system. The marker array-specific coordinate system can be linked in particular with an object on which the markers are secured or mounted, or can be arranged in a stationary fashion in relation to said object. The object can be, e.g., a carrier device for the markers. A movement of the object and thus also of the marker array-specific coordinate system can then also lead to the movement of the markers, although there is no variation of the relative position of the markers with respect to one another in the marker array-specific coordinate system.

It is thus possible that although such a movement of the object with the markers leads to a position variation of the markers in a coordinate system that is different than the marker array-specific coordinate system, there is no position variation of the markers in the marker array-specific coordinate system.

In this case, it is possible for at least one marker to be mounted in a stationary fashion and one marker in a movable fashion in relation to the marker array-specific coordinate system on the object. As explained in even greater detail below, at least one marker of a marker array including a plurality of markers can be a marker that is movable in relation to the marker array-specific coordinate system, wherein the remaining markers can be arranged in a stationary fashion relative to one another and/or in a stationary fashion with respect to the marker array-specific coordinate system.

The change of the relative position can be effected with a change of the position of one marker or with a position change of at least two markers, in particular in the marker array-specific coordinate system.

In this case, the control signal can additionally be generated only if the relative position change is present for longer than a predetermined time duration, e.g., for at least one second, and the position change is thus identifiable for longer than the predetermined time duration.

Since, with the optical position detection system, the position of markers can be determined with high accuracy, in particular also in the generated image, the change of the relative position of said markers with respect to one another can also be detected in a simple and reliable manner. This in turn advantageously leads to a reliable and robust generation of the control signal.

Alternatively or cumulatively, a control signal can be generated depending on a change of a number of imaged markers. In this regard, a control signal can be generated for example if the number of markers identified in the first image is more or fewer than the number identified in the at least one further image. In addition to the identification of markers, a type or an identifier of the marker can also be identified in an image-based manner. In this regard, by way of example, it is possible to identify whether an imaged marker corresponds to a predetermined marker type, particularly if markers of different marker types are used. Furthermore additionally it is also possible to identify a type or an identifier of a marker array to which one or more identified markers belong.

The change of the number may be caused for example by the revealing or the concealing of one or more markers, in particular of a marker array. Concealing can mean that a marker is transferred from a state detectable by the optical detection system to a non-detectable state. Revealing can mean that a marker is transferred from a state not detectable by the optical detection system to a detectable state. The concealing and revealing can be effected by manual actuation of at least one marker, for example by a body part, e.g., a finger.

In this case, the control signal can additionally be generated only if the change of the number is present for longer than a predetermined time duration, e.g., for at least one second, and the changed number is thus identifiable for longer than the predetermined time duration.

In this regard, by way of example, a control signal can be generated if a number of markers, in particular markers of a marker array, change in a predetermined manner, in particular if the number increases or decreases by a predetermined absolute value.

By way of example, the control signal can be generated only if the number decreases, for example by a predetermined number, in particular by the number one. This advantageously results in more reliable generation of control signals since the risk of unintentional generation of the control signal is reduced. It is furthermore evident in an advantageous manner that mutually different control signals are generated which can be assigned for example to mutually different changes of the number.

Furthermore alternatively or cumulatively, the control signal can be generated only if, in the case of a reduction of the number of markers, one or at least two markers is/are identified in the image. As a result, an operational reliability can advantageously be increased since no control signal is generated in the event of the markers being moved out of the detection region of the optical position tracking system.

Furthermore alternatively or cumulatively, the control signal can be generated depending on a change of an absolute position of at least one imaged marker, in particular a marker of an identified marker array. The absolute position can be for example a position in a global reference coordinate system, e.g., in a coordinate system of the optical detection device.

Furthermore, by way of example, a movement trajectory, in particular a movement trajectory in the global reference coordinate system or a movement trajectory of the relative movement, of at least one marker can be determined, wherein the control signal is generated if the movement trajectory deviates from a predetermined movement trajectory by not more than a predetermined amount. A deviation can be determined for example as a spatial distance between two movement trajectories, and/or depending on a correlation between two movement trajectories. For example, a deviation can be determined by a spatial distance between reference points on the movement trajectory, in particular in a state of the minimum distance between the movement trajectories (best fit).

In this case, information concerning predetermined movement trajectories and also the assignment of these predetermined trajectories to a control signal can be predetermined and stored, for example in a storage device of a system for generating a control signal. During operation, a determined or detected movement trajectory can then be compared with these stored movement trajectories, wherein the control signal is generated if the deviation does not exceed the predetermined amount.

By way of example, a predetermined movement trajectory can correspond to a trajectory required for carrying out a double click with a mouse button. Moreover, a predetermined movement trajectory can correspond to a predetermined circular or partially circular movement.

It is furthermore possible for the control signal to be generated only if the movement along the movement trajectory of the at least one marker has predetermined movement properties, for example a predetermined movement speed or path distance. Alternatively or cumulatively, the control signal can be generated only if the movement along the movement trajectory takes place within a predetermined time duration.

This advantageously results in a reliable and simple generation of a control signal. Furthermore, mutually different control signals can be assigned to mutually different movement trajectories. This advantageously has the result that the possibilities for use of the method are advantageously increased.

In this case, the change of the number and/or the position change can be a necessary condition which has to be met for generating the control signal. However, it is possible that in addition to meeting this necessary condition, at least one further condition must also be met in order to generate the control signal.

In this case, different control signals can be assigned to mutually different number changes, position changes, numbers following the change and/or positions, in particular relative positions of at least two markers, following the change and/or marker trajectories.

If no markers or markers insufficient for determining a position change and/or change of the number are identified, then no control signal can be generated.

The method advantageously enables a control signal to be generated simply and in a manner that can be carried out with little manual effort. In particular, a control signal can be generated by a user with the aid of an optical position detection system that has possibly already been activated, in particular without the need for the actuation of a device different therefrom for generating a control signal.

In a further exemplary embodiment, the control signal is generated if the relative position changes in a predetermined manner. By way of example, the control signal can be generated only if one or a plurality of property(-ies) correspond(s) to the position change of one or respectively a plurality of predetermined property(-ies). A property can be for example a predetermined direction, a predetermined trajectory or a predetermined path distance.

It is conceivable for mutually different control signals to be assigned to mutually different predetermined changes of the relative position. In this regard, by way of example, a first control signal can be generated if the relative position varies by a first absolute value, wherein a second control signal, different than the first control signal, can be generated if the position varies by a second predetermined amount.

This advantageously results in an increased operational reliability since the risk of the unintentional generation of a control signal on account of, e.g., an unintentional variation of the relative position is minimized. At the same time, it is evident in an advantageous manner that different control signals can be generated reliably. In this regard, e.g., different operating modes can be activated with different control signals. Moreover, one operating mode or different operating modes can be activated or deactivated with different control signals. Furthermore, stateful activation signals can advantageously be generated as well.

In a further exemplary embodiment, the position change is effected with a relative movement along a linear trajectory.

In a further exemplary embodiment, alternatively or additionally the position change is effected with a relative movement along a trajectory in the shape of a circle arc or with rotation of at least one marker. In this case, the position change along a trajectory in the shape of a circle arc thus includes the position change which takes place from the rotation of at least one marker about a rotation axis, wherein the rotation axis can correspond to an axis of symmetry or central axis of the marker. In this regard, it is possible for the marker to be embodied as circular or disk-shaped. Alternatively, the rotation axis can also be different than the axis of symmetry or central axis. In particular, the rotation axis can be arranged parallel, but spatially offset, with respect to the axis of symmetry.

It goes without saying that the position change can also be effected with other trajectories, for example trajectories having a preselected shape. The relative movement along a linear trajectory or trajectory in the shape of a circle arc advantageously results, however, in a simple and thus reliable image-based identification of the position change.

In a further exemplary embodiment, the position change is effected with manual actuation of at least one marker. In this regard, the actuatable marker can be mounted for example in such a way that it is movable relative to at least one further marker, in particular of the marker array explained above. By way of example, the marker can be mounted in a linearly movable fashion. Alternatively or cumulatively the marker can be mounted in a rotatable fashion. Furthermore alternatively or cumulatively the marker can be mounted in a tiltable fashion. In this case, the linear movement and/or the rotational movement and/or the tilting movement can be brought about by a user, for example by manual actuation. Furthermore by way of example the marker can be moved out of an initial position with the manual actuation. The initial position is explained in even greater detail below.

This advantageously results in a simple and, particularly with the use of passive markers, energy-saving generation of a control signal.

In a further exemplary embodiment, at least one marker is moved out of an initial position, wherein a restoring force/restoring moment for moving the marker into the initial position is generated in a different position than the initial position. The movement of the marker out of the initial position can be referred to as first position change. Said first position change can be produced with manual actuation. The initial position can thus be a stable position of the marker, wherein positions different than the initial position can be unstable positions.

The restoring force/restoring moment can be generated in particular by at least one restoring element. The restoring element can for example be embodied as a spring or include a spring. Without further forces/moments acting on the marker, the restoring force/restoring moment causes a movement of the marker into the initial position or into one of a plurality of initial positions. The initial position can thus denote a position of the marker in which no restoring force/restoring moment acts on the marker.

The restoring force/restoring moment can lead to a further position change, in particular to a position change for reversing/cancelling the first position change.

In such a case, the marker is embodied as a so-called pushbutton marker. The latter, after a deflection from the initial position, can return to the initial position again without additional manual actuation.

As a result, stateless activation signals, in particular, can be generated. In this regard, an activation signal can be generated, e.g., after the movement of the marker from the initial position or after the return to the initial position. A stateless activation signal can thus be an activation signal which is independent of the end position after a deflection. However, with a pushbutton marker it is also possible to generate a first activation signal when the marker is moved from the initial position, and to generate an activation signal different therefrom, e.g., a deactivation signal, when the marker has returned to the initial position.

In an alternative exemplary embodiment, at least one marker moves from an initial position into an end position, wherein no restoring force/restoring moment, in particular with a restoring element, for moving the marker into the initial position is generated in the end position. However, it is possible for a restoring force/restoring moment, in particular with a restoring element, for moving the marker into a further initial position is generated in the end position. The initial position and also the end position can thus be stable positions of the marker.

In such a case, the marker is embodied as a so-called switch marker. The latter, after a deflection from the initial position, cannot return to said initial position again without additional manual actuation. In particular, various stable positions can exist for the marker.

As a result, stateful activation signals, in particular, can be generated. In this regard, an activation signal can be generated after the end position has been reached. If a plurality of end positions exist, then end position-specific state signals can be generated.

A stateful activation signal can thus be an activation signal which is dependent on the end position after a deflection.

Both in the case of a pushbutton marker and in the case of a switch marker, however, it is possible to generate a control signal upon a change of the relative position, e.g., by virtue of a signal level value changing. A superordinate unit, e.g., an evaluation device, can then evaluate the corresponding change and generate a corresponding activation signal. In this regard, by way of example, a stateless control signal can be generated by virtue of the signal level value changing upon each change of the relative position. A stateful control signal can be generated by virtue of the signal level value changing only upon predetermined changes of the relative position. It goes without saying, however, that other forms of signal evaluation are also possible.

In a further exemplary embodiment, a marker-based position determination is interrupted or ended if the relative position between at least two markers changes, in particular in a predetermined manner. In other words, a so-called position determination mode is interrupted or ended. The marker-based position determination that is effected in a position determination mode has already been explained in the introduction. In the position determination mode, output signals of the optical detection device are used to determine a position of the markers or of the marker array, in particular in a global reference coordinate system. Moreover, the position of the object on which the markers are secured or mounted can be determined in the position determination mode. In other words, in the position determination mode, it is possible to determine a position of the marker array-specific coordinate system in a coordinate system different therefrom.

The marker-based position determination can be carried out in particular if the markers are located in a predetermined determination operation relative position. In this case, a plurality of determination operation relative positions can exist. In such a case, the marker-based position-bearing determination can be interrupted or ended if a position change out of the/a determination operation relative position takes place or if a predetermined position change, which can also be referred to as a position change for deactivating the position determination, takes place.

In addition, a control signal can then be generated, as explained above, upon the interrupting or upon the ending. Said control signal can be for example a deactivation signal for the position determination mode.

Moreover, a control mode can additionally be activated. For example, an activation signal for a control mode can be generated. In the control mode, output signals of the optical detection device are used to generate control signals, e.g., activation or deactivation signals.

The marker-based position determination can be continued or begun if a position change into the determination operation relative position takes place or if a further predetermined position change, which can also be referred to as a position change for activating the position determination, takes place. In this case, the control mode can additionally be deactivated. For example, a deactivation signal for a control mode can be generated.

It is thus possible that control signals which are generatable depending on a change of a number of imaged markers and/or depending on a change of the absolute position of at least one imaged marker and/or depending on a relative position change between at least two imaged markers are generated only if a control mode is activated, for example if the markers are not located in a determination operation relative position. In this case, it is not possible to carry out a marker-based position determination.

Accordingly, it is not possible to generate such control signals if a position determination mode is activated, e.g., if the markers are located in a determination operation relative position. In this case, it is possible to carry out a marker-based position determination for the object on which the markers are arranged or mounted.

As a result, an operational reliability during the position determination is advantageously increased.

In a further exemplary embodiment, mutually different changes are assigned mutually different control signals. In this regard, different changes of the number and/or different changes of the relative position can be assigned mutually different control signals.

Furthermore additionally, mutually different marker arrays following the change can be assigned mutually different control signals. In this case, it is possible to identify a marker array following the change, for example in an image-based manner.

In this regard, different control signals can be assigned to different changes, in particular marker array changes. Alternatively or cumulatively, different control signals can also be assigned to different marker arrays resulting from the change, e.g., different control signals can be generated depending on which and how many markers have been concealed and/or revealed and/or have varied their position. Different marker arrays can be characterized for example by a different number of markers and/or different relative positions of at least two markers of the marker array with respect to one another.

This advantageously has the result that mutually different control signals can be generated, as a result of which the possibilities of use for the method according to an aspect of the disclosure are advantageously increased.

In a further exemplary embodiment, a marker array is identified depending on the identified markers. The marker array can be in particular a marker array for securing to an object to be detected by the optical position detection system. The markers of the marker array are thus not arranged on mutually different objects.

The marker array includes at least two markers. Typically, the marker array includes at least four markers. Mutually different marker arrays can differ in particular in the marker types of the markers in the marker array, the arrangement of the markers in the marker array relative to one another, and/or in different numbers of markers. In this case, it may be possible to configure a marker array in such a way that the latter is identifiable in an image-based manner if all the markers of the marker array are imaged in the image. Alternatively or cumulatively, it is possible to configure the marker array in such a way that the marker array is identifiable in an image-based manner if not all of the markers of the marker array, for example all except for one marker of the marker array, are imaged in the image.

In this case, markers of the marker array can be arranged such that they are non-movable relative to one another, for example on/at a carrier device of the marker array. Alternatively, it is possible for at least one marker of the marker array to be arranged in a movable manner relative to the further markers of the marker array, wherein the further markers of the marker array are arranged in a non-movable manner relative to one another.

Furthermore, it is possible for the marker array to include at least one movable element, for example a covering element for concealing at least one marker of the marker array.

Furthermore, the control signal is generated depending on a change of the number of imaged markers of said marker array and/or depending on a relative position change between at least two markers of said marker array. Moreover, the control signal can be generated depending on a marker array resulting from the change. This has already been explained above.

Alternatively or cumulatively, the control signal can be generated depending on a position change of the marker array.

Such a marker array advantageously enables a control signal to be generated in a reliable manner, in particular with a user action to be carried out in a simple manner, for example with concealing or revealing at least one marker of the marker array and/or with varying a position of at least one marker of the marker array relative to further markers of the marker array.

In a further exemplary embodiment, the controllable device is a positioning device. A positioning device can serve, as explained above, for the positioning of an object to be positioned. The latter can be arranged or secured for example on an end effector of the positioning device.

With the positioning device, it is thus possible to set a spatial position and/or a spatial orientation of the object to be positioned, in particular in a predetermined reference coordinate system.

An object to be positioned can be a microscope or a part of a microscope. In this case, in particular, the positioning device can be or include a stand for mounting a microscope. It is possible that the microscope is secured to a free end of the stand, in particular in movable fashion, e.g., in pivotable fashion. In this case, the stand is embodied in such a way that a movement of the microscope in space is made possible, in particular with at least one degree of freedom, typically with six degrees of freedom. The stand can include at least one drive device, typically a plurality of drive devices, for moving the microscope. Such a drive device can denote a device for generating a drive force or a drive moment. Such a drive device can be a servo motor, for example. Of course, the stand can also include means for transmitting forces/moments, e.g., gear units. In particular, it is possible to drive the at least one drive device of the stand in such a way that the microscope carries out a desired movement and thus a desired position change in space or adopts a desired position in space. In this case, a position denotes a position and/or an orientation, in particular in a reference coordinate system. Methods for controlling the at least one drive device depending on a desired position and a kinematic structure of the stand are known here to the person skilled in the art.

Alternatively, the positioning device can be a coordinate measuring device or a part of a coordinate measuring device. The coordinate measuring device can be in particular a coordinate measuring device of gantry design, of stand design or of some other design. In this case, the coordinate measuring device can include at least one movable part, typically a plurality of movable parts, serving for the position change and thus for the positioning of a measuring device.

In this case, the object to be positioned can be a measuring device, e.g., a measuring head or a measuring head system, of a coordinate measuring device. The measuring device can be in particular a measuring device that measures with contact or a non-contact measuring device. The measuring device can thus serve for generating measurement points during the measurement of a measurement object, wherein the measurement can be effected in non-contact fashion, in particular optically, or with contact, in particular in tactile fashion.

By way of example, the coordinate measuring device can include at least one stand element which is movable along a longitudinal axis of a reference coordinate system. Furthermore, a coordinate measuring device can include a crossbar arranged on the at least one stand element. Furthermore, a sleeve of the coordinate measuring device can be moved along the crossbar, wherein said sleeve is mounted on the crossbar and is moved along a transverse axis during this movement. Furthermore, the measuring device can be mounted on the sleeve in a movable manner, wherein the latter can carry out a movement along a vertical axis. Here, the vertical axis can be oriented parallel and counter to the direction of a gravitational force. The longitudinal axis and the transverse axis can span a reference plane oriented orthogonally with respect to the vertical axis.

This advantageously results in a simplified control of a positioning device.

In a further exemplary embodiment, the control signal is an activation signal for activating a predetermined operating mode of the controllable device. Alternatively, the control signal is a deactivation signal for deactivating a predetermined operating mode of the controllable device. It is possible, of course, for different control signals to be generatable, in particular position change-specific control signals. In other words, different position changes of the relative position between at least two markers can generate mutually different control signals. In particular, a first control signal can be an activation signal, wherein a further control signal, which is different than the first control signal, can be a deactivation signal. Exemplary operating modes are explained in even greater detail below.

In particular, the controllable device can perform at least one operating mode-specific function in an activated operating mode. If the operating mode is deactivated, then the controllable device cannot perform said operating mode-specific function.

This advantageously results in a simple, but reliable activation and deactivation of different operating modes of the controllable device.

Furthermore, the control signal can also be a signal for controlling the operation of the controllable device. In particular, the control signal can be used depending on an activated operating mode for the control of operation. In other words, if a specific operating mode is activated, then the control signal can be an operating mode-specific control signal. By way of example, if a position tracking mode is activated, this mode being explained in even greater detail below, then the control signal can serve for controlling a spatial position of an object to be positioned. In other words, a control signal can be interpreted in an operating mode-specific manner.

In this regard, it is possible, for example, for an activation control signal to serve for activating an operating mode. In the activated operating mode, a deactivation control signal can serve for deactivating the operating mode. Said deactivation signal can be different from the activation signal, but also identical to said activation signal. In the activated operating mode, control signals which are different from the deactivation signal and which are generated depending on a change of the relative position between two markers can then serve for controlling operation of the controllable device or parts thereof.

Alternatively or cumulatively, in particular in an activated operating mode, signals which are not generated depending on a change of the relative position between two markers can serve for controlling operation, e.g., signals which are generated depending on a position change of an instrument, a marker or a marker array.

In a further exemplary embodiment, the predetermined operating mode is a position tracking mode. A position tracking mode has already been explained above. In an activated position tracking mode, a positioning device can carry out a position change of an object to be positioned that is identical to the position change of an instrument, a marker or a marker array or corresponds to a scaled position change of the instrument, the marker or the marker array. It is possible to determine a position change of a marker or a marker change. If the marker or the marker array is arranged on an instrument, a position change of the instrument can thus be determined as well. Furthermore, the positioning device can be driven depending on the position change of the instrument, the marker or the marker array in such a way that the object to be positioned carries out the same or a scaled position change. In the activated position tracking mode, the control signal for controlling the positioning device can be, in particular, a control signal that is not generated depending on a change of the relative position between two markers, but rather a control signal that is generated depending on the position change of the instrument, the marker or the marker array.

This advantageously results in a simplified control of the spatial movement of the positioning device, in particular for positioning an object to be positioned, e.g., a microscope or a measuring device.

In a further exemplary embodiment, the operating mode is a measuring mode. Said measuring mode has already been explained above. In particular, measurement points for the measurement of a measuring object can be generated and stored in an activated measuring mode.

This advantageously results in simplified operation of a coordinate measuring device.

In a further alternative exemplary embodiment, the operating mode is an illumination change mode or an illumination intensity variation mode or a camera zoom mode or a menu operation mode or an input mode. These modes have already been explained in greater detail above. This advantageously results in further simplified operational control of a controllable device.

The latter can include in particular at least one illumination device, for example a light source. In the illumination change mode, it is possible to control/set switching on, switching off of the at least one illumination device or variation of an illumination scenario with the at least one illumination device depending on the control signal. A corresponding control signal can be generated in particular depending on a change of the relative position between two markers.

In an illumination intensity variation mode, an illumination intensity of the at least one illumination device can be controlled depending on the control signal. A corresponding control signal can be generated in particular depending on a change of the relative position between two markers, alternatively depending on a position change of the instrument, the marker or the marker array.

Moreover, the controllable device can include a camera, which can also be referred to as an image capture device. In a camera zoom mode, a zoom of the camera can be set depending on the control signal. A corresponding control signal can be generated in particular depending on a position change of the instrument, the marker or the marker array rather than depending on a change of the relative position between two markers.

In a menu operation mode, as explained above, depending on the control signal, menu items or elements can be selected with a corresponding control signal and can optionally be actuated simultaneously or with a control signal generated anew.

By way of example, in an input mode, a selection or actuation means, e.g., a cursor, can be operated depending on the control signal. In the activated menu operation mode, a selection or actuation signal can be generated, e.g., depending on a change of the relative position between two markers. In the activated menu operation mode, a control signal for varying the position of an input, selection or actuation means can be generated depending on a position change of the instrument, the marker or the marker array, rather than depending on a change of the relative position between two markers.

By way of example, it is possible to represent virtual input means, e.g., a keyboard, a menu or the like, and selection or actuation means, which are controlled correspondingly.

In a further exemplary embodiment, the control signal is an activation signal for storing a current position of an instrument and/or a marker or a marker array. Alternatively or cumulatively, the control signal is an activation signal for storing a current position of an object to be positioned by the positioning device. As a result, it is advantageously possible to remember positions of a marker, a marker array, an instrument or an object to be positioned, for example in order to set them again at a temporally later point in time, in particular with corresponding driving of the positioning device. In this case, a system for generating a control signal can include a storage device that serves for storing the current position.

In addition, a marker array for generating a control signal with an optical position detection system is provided. The marker array has already been explained above. In particular, the marker array includes at least one marker or at least two markers for detection by an optical position detection system.

According to an aspect of the disclosure, the marker array includes at least one means for changing the number of detectable markers of the marker array. Alternatively or cumulatively, the marker array includes at least one means for changing a relative position between at least two markers of the marker array.

Furthermore, the marker array can include at least one securing means for securing the marker array to an object. Furthermore, the marker array can include at least one carrier device, wherein the markers of the marker array can be arranged in/on the carrier device.

The means for changing the number of detectable markers can be arranged and/or embodied in such a way that at least one marker can be put into a state that is not detectable by the optical position detection system. Furthermore, said means can be embodied in such a way that the at least one marker can also be put into a detectable state. By way of example, the means for changing the number can include at least one covering element, wherein in a first state the covering element covers at least one marker of the marker array in such a way that this is not detectable by the optical position detection system. In a second state, it is possible for the at least one marker not to be covered. However, it is also conceivable for the means for changing the number of detectable markers to be a means for changing a position of at least one marker. In this regard, e.g., the means can be embodied in such a way that at least one marker of the marker array can be put into a non-detectable state with a position change, for example a rotation, a linear movement or a tilting. It is thus possible for the means for changing the number of detectable markers to form the means for changing the relative position, or vice versa. Such a marker array advantageously results in a simple and reliable generation of a control signal.

In a further exemplary embodiment, the marker array includes at least one covering device for covering at least one marker of the marker array. This and corresponding advantages have already been explained above.

In a further exemplary embodiment, the marker array includes at least one guide device for guiding the movement of at least one movable marker of the marker array. The guide device can be or include a bearing device. By way of example, the guide device can guide a linear movement, a rotational movement or a tilting movement. It goes without saying that it is also possible that both a rotational movement and a linear movement can be guided by the at least one guide device. In the case of such a movement, a rotational movement can be superimposed on a linear movement, or vice versa. A movement with one or a plurality of a maximum of six degrees of freedom of movement can thus be guided with the guide device. This advantageously results in a simple and reliable variation of the relative position between at least two markers of the marker array.

In a further exemplary embodiment, the marker array includes at least one means for defining a position of the at least one movable marker. By way of example, the at least one movable marker can be moved along a predetermined movement trajectory. The means for defining the position can define for example end positions of the movable marker and optionally also one or a plurality of positions of the movement trajectory between the end positions. The marker can be locked, for example, in these defined positions. In particular, a means for defining a position can be embodied as a stop element or as a latching element or can include such elements. This advantageously results in a reliable setting of positions of the at least one movable marker. This in turn also enables the reliable setting of changes of the relative position in predetermined ways.

In this regard, by way of example, a first control signal can be generated if the movable marker is moved from a first position into a second defined position. A further control signal can be generated if the marker is moved from the first defined position into a further defined position, which is different than the second defined position.

In addition, a system for generating a control signal with an optical position detection system is provided. The system includes at least one marker, at least one optical detection device of the optical position detection system and at least one evaluation device. In this case, the at least one evaluation device can be a computing device, wherein the computing device can include or be embodied as at least one microcontroller, for example.

In particular, the system can include at least one marker array in accordance with one of the exemplary embodiments described in this disclosure.

At least two images of at least one spatial region are generatable with the at least one optical detection device, wherein markers are identifiable in the images with the at least one evaluation device.

According to an aspect of the disclosure, with the at least one evaluation device, a control signal is generatable depending on a position change of at least one imaged marker. In particular, the control signal is generatable if a relative position between at least two markers changes.

The system advantageously serves for carrying out a method for generating a control signal in accordance with one of the exemplary embodiments described in this disclosure. In other words, the system is configured in such a way that such a method can be carried out by the system.

A controllable system is also provided, wherein the controllable system comprises at least one system for generating a control signal in accordance with one of the exemplary embodiments described in this disclosure and at least one controllable device. At least one control signal is generatable with the system for generating the control signal, wherein operation of the controllable device is controllable with the control signal.

This advantageously results in a controllable system with an optical position detection device, which system can be operated simply and temporally rapidly.

A description is also given of a program which, when executed on or by a computer, causes the computer to carry out one, a plurality, or all of the steps of the method disclosed in this disclosure for generating a control signal for a controllable device with an optical position detection system. Alternatively or cumulatively, a program storage medium is described on or in which the program is stored, in particular in a non-temporary form, i.e., in a permanent form. Alternatively or cumulatively, a computer which includes this program storage medium is described. Furthermore alternatively or cumulatively, a description is given of a signal, for example a digital signal, which codes information representing the program and which includes code means adapted to carrying out one, a plurality or all of the steps of the method disclosed in this disclosure for generating a control signal for a controllable device with an optical position detection system. The signal can be a physical signal, for example an electrical signal, which in particular is generated technically.

Furthermore, the method for generating a control signal for a controllable device with an optical position detection system can be a computer-implemented method. In this regard, for example, one, a plurality or all of the steps of the method can be carried out by a computer. One exemplary embodiment of the computer-implemented method is the use of the computer for carrying out a data processing method. For example, the computer can include at least one computing device, in particular a processor, and for example at least one storage device, in order to process the data, in particular technically, for example electronically and/or optically. A computer can in this case be any kind of data processing appliance. A processor can be a semiconductor-based processor.

BRIEF DESCRIPTION OF THE DRAWINGS

The disclosure will now be described with reference to the drawings wherein.

DESCRIPTION OF EXEMPLARY EMBODIMENTS

Identical reference signs hereinafter denote elements having identical or similar technical features.

Figure 1:
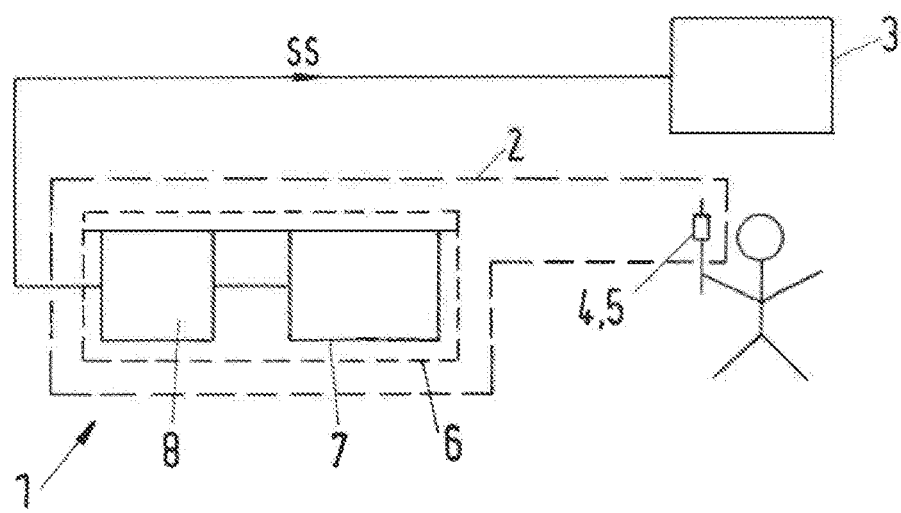
FIG. 1 shows a schematic block diagram of a controllable system including a system for generating a control signal according to an exemplary embodiment of the disclosure.

FIG. 1 shows a schematic block diagram of a controllable system 1. The controllable system 1 includes a system 2 for generating a control signal SS. Furthermore, the controllable system 1 includes a controllable device 3, for example a positioning device or a coordinate measuring device.

Figure 3A:
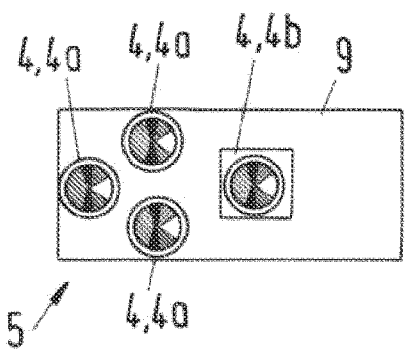
FIG. 3A shows a schematic plan view of a marker array in a fully detectable state.

The system 2 for generating a control signal SS includes at least one marker 4 or a marker array 5, wherein the marker array 5 can include a plurality of markers 4 (see, e.g., FIG. 3A). Furthermore, the system 2 for generating a control signal SS includes an optical position detection system 6. The optical position detection system 6 includes at least one optical detection device 7, for example one camera or a plurality of cameras of a stereoscopic camera system. Furthermore, the optical position detection system 6 includes an evaluation device 8, wherein said evaluation device 8 can include a microcontroller or can be embodied as such.

With the optical detection device 7, an image of a spatial detection region of the optical detection device is generatable, in particular a two-dimensional image. In this case, the optical detection device 7 is signal- and/or data-technologically connected to the evaluation device 8. Depending on/on the basis of the image data generated by the optical detection device 7, the evaluation device 8 can identify markers 4 imaged in the image. Known methods of image processing can be employed for this purpose.

Furthermore, with the evaluation device 8, a control signal SS can be generated depending on a change of a number of imaged markers 4 and/or depending on a position change of at least one imaged marker 4. Typically, the control signal SS can be generated depending on a change of a relative position between at least two markers 4 of the marker array 5.

In this case, the evaluation device 8 can include a plurality of partial evaluation devices, wherein, e.g., a first partial evaluation device, depending on the image data generated, can determine a position of the markers 4 or of the marker array 5 in a coordinate system of the optical detection device 7 or in a reference coordinate system. A further partial evaluation device can generate the control signal SS, as explained above. In this case, the partial evaluation devices can be embodied as a common evaluation device or as separate evaluation devices.

The control signal SS can be transmitted to the controllable device 3. For this purpose, the controllable device 3 can be signal- and/or data-technically connected to the evaluation device 8. Operation of the controllable device can be controlled depending on the control signal SS.

Typically, the control signal is an activation signal for activating an operating mode of the controllable device 3 or a deactivation signal for deactivating an operating mode of the controllable device 3. Exemplary operating modes have already been explained above. Exemplary controllable devices 3 have likewise been explained. If the controllable device 3 is for example a positioning device, in particular a robot, then a position tracking mode of the controllable device 3 can be activated or deactivated. If the controllable device 3 is a coordinate measuring machine, for example, then a measurement mode of the controllable device 3 can be activated or deactivated.

Figure 2:
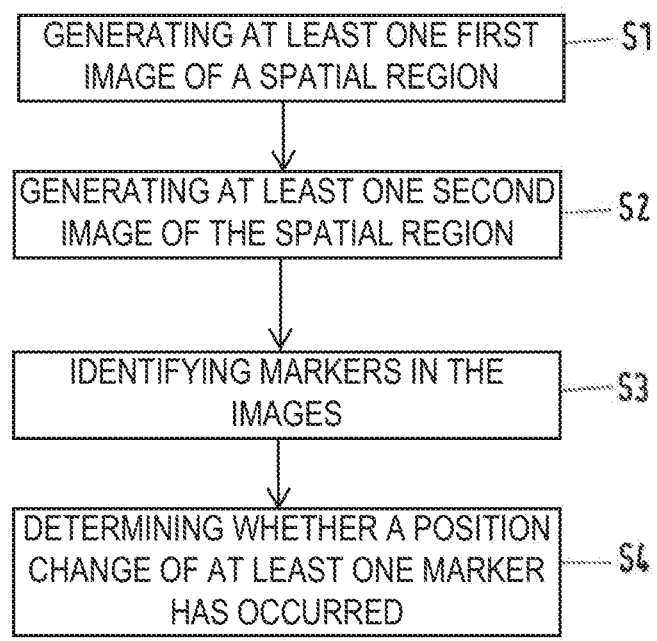
FIG. 2 shows a schematic flow diagram of a method according to an exemplary embodiment of the disclosure.

FIG. 2 shows a schematic flow diagram of a method according to the disclosure for generating a control signal SS (see FIG. 1) for a controllable device 3 with an optical position detection system 2.

In a first step S1, at least one first image of a spatial region, in particular the detection region of the optical detection device 7, is generated.

In a second step S2, at least one second image of the spatial region is generated.

In a third step S3, markers 4 are identified in the images.

In this case, the third step S3 can be carried out simultaneously for both images or separately for both images.

A fourth step S4 involves determining whether a position change of at least one identified marker has occurred. In particular, this involves determining whether a relative position between two markers 4 has varied. In this case, the position change can be determined in an image coordinate system or a coordinate system of the optical detection device 7 or in a reference coordinate system different therefrom. It is possible for the position change to be effected with a manual actuation of the at least one marker 4. Moreover, the position change can be caused by a restoring element of the marker array 5.

In particular, it is possible to determine whether the relative position between at least two markers 4 of a marker array 5 has changed. For this purpose, in the third step S3, a marker array 5 can be identified depending on the identified markers 4. For this purpose, by way of example, marker-specific identifiers can be determined, in particular in an image-based manner, wherein the marker array 5 can then be identified depending on the marker-specific identifiers. It goes without saying that, depending on the identifiers, it is also possible to determine which markers 4 of the marker array 5 have moved.

Furthermore, it is possible to determine whether the relative position has changed in a predetermined manner. In particular, it is possible to determine for example whether the relative position has changed along a linear trajectory. Alternatively, it is possible to determine whether the position change has been effected with a relative movement along a trajectory in the shape of a circle arc or with a rotation of at least one marker. As explained above, the position change along a trajectory in the shape of a circle arc can include a position change effected from the rotation of at least one marker about a rotation axis, wherein the rotation axis can correspond to or be different than an axis of symmetry of the marker.

Furthermore, here, too, it is possible to determine a path distance covered along the trajectory and/or a rotational angle covered during a rotation.

If it is detected that a relative position between at least two markers 4 with respect to one another has changed or that the relative position has changed in a predetermined manner, then the control signal SS can be generated. Different position changes can be assigned different control signals SS. Different control signals can activate or deactivate different operating modes, for example.

Furthermore, e.g., in a fifth step (not illustrated), after detecting a change of the relative position, it is possible to determine a state of the marker array 5, in particular in an image-based manner. Depending on which marker(s) 4 of the marker array 5 has (have) been moved and the way in which the marker(s) 4 has (have) been removed, a plurality of states of the marker array 5 can exist. Each of these states can then be assigned a control signal SS. Consequently, a control signal SS can be generated if a position change has been effected and the resulting state of the marker array 5 following the position change corresponds to a predetermined state. In this case, the assignment of control signals to states of the marker array 5 can be predetermined and be stored for example in a storage device of the system 2. Said assignment can be retrievable by the evaluation device 8, in particular.

Alternatively or cumulatively, in the fourth step S4, a change of a number of imaged markers 4 can be determined. In this case, too, the markers 4 can be markers of a marker array 5.

A control signal SS can be generated if the number of detectable markers 4 has changed. Alternatively, a control signal SS can be generated if the number of identified markers has changed in a predetermined manner. Different changes of the number can be assigned different control signals SS.

Moreover, it is possible to determine a state of the marker array 5 following the change of the number. In this case, different states of the marker array 5 can exist following the change of the number, in particular depending on the number resulting from the change and also depending on the arrangement of the still identifiable markers 4. A control signal SS can thus be generated if the number has changed by a predetermined absolute value and the state of the marker array 5 following the change corresponds to a predetermined state.

Alternatively or cumulatively, it is possible, in the fourth step S4, to determine a position change of at least one marker 4, in particular of the marker array 5, in an image coordinate system, a coordinate system of the optical detection device 7 or in a reference coordinate system. Furthermore, a trajectory of the at least one marker 4 can be determined depending on said position change. A control signal SS can be generated if the trajectory of the marker 4 determined in this way deviates from a predetermined trajectory by not more than a predetermined amount. In this case, an assignment of predetermined trajectories and control signals SS can be previously known and, e.g., likewise stored in the storage device explained above. A control signal SS assigned to a predetermined trajectory is thus generated in this case if the trajectory of a marker 4 determined at the operating time deviates from said predetermined trajectory by not more than a predetermined amount.

FIG. 3A shows a schematic plan view of a marker array 5 for explaining the generation of a control signal SS depending on a change of a number of detectable markers 4. The marker array 5 includes a carrier device 9, for example a carrier body. Four markers 4 are arranged or secured on the carrier device 9. In this case, the marker array 5 includes four markers 4a which are non-movable relative to one another, and which can also be referred to as rigid markers 4a. Said rigid markers 4a are markers 4 of a first marker group of the marker array 5. Furthermore, the marker array 5 includes a further marker 4b. Said marker 4b is a marker 4 of a second marker group of the marker array 5.

In FIG. 3A, the markers 4 are produced as disks having a colored surface, wherein a grayscale value of the colored surface changes along the surface in a predetermined manner. This enables a simple image-based identification of the markers 4. It goes without saying, however, that other exemplary embodiments of markers 4 can also be used.

FIG. 3A illustrates the marker array in a fully detectable state. In this case, the markers 4a of the first marker group serve for the determination of the position of the marker array 5 with the optical position detection system 2.

Figure 3B:
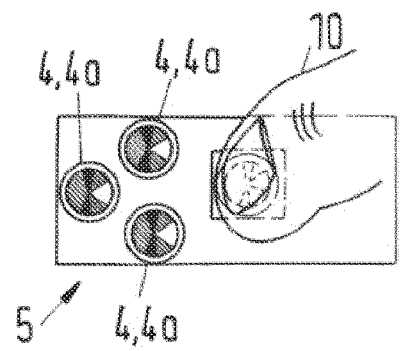
FIG. 3B shows a schematic plan view of the marker array illustrated in FIG. 3A in a partly detectable state.

In FIG. 3B, the marker array 5 illustrated in FIG. 3A is illustrated in an only partly detectable state. In this case, the illustration shows that the marker 4b of the second group is concealed, by way of example by a user's thumb 10 in FIG. 3B. On account of being covered by the thumb 10, the marker 4b of the second group cannot be imaged by the optical detection device 7.

A number of markers 4 that are identifiable in the image thus decreases when a change is made from the state illustrated in FIG. 3A to the state illustrated in FIG. 3B.

The illustration shows that the number of identifiable markers 4 decreases from the number four to the number three. If such a decrease is detected, then a control signal SS can be generated.

FIG. 3B illustrates that the marker 4b is covered by a user's thumb 10. It goes without saying, however, that it is also possible for the marker array 5 to include a means for covering, in particular a covering device, which can put the marker 4b into a state not detectable by the detection device 7. By way of example, the covering device can include a movable, e.g., pivotable, element, which can be secured to the carrier device 9 in a movable fashion. Said covering device can be actuatable by a user in order to put the marker 4b into a non-detectable state or into a detectable state.

Figure 4A:
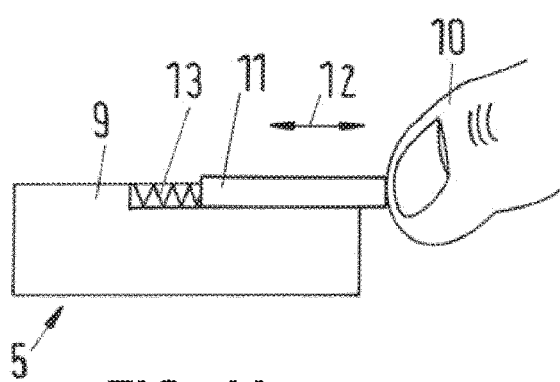
FIG. 4A shows a schematic side view of a marker array in accordance with a first exemplary embodiment of the disclosure.

FIG. 4A shows a schematic side view of a marker array 5 in accordance with one exemplary embodiment of the disclosure. The carrier body 9 for the markers 4a of a first marker group is illustrated. A movable element 11 mounted on the carrier device 9 in a linearly movable fashion is also illustrated. The linear movement is represented by way of example by an arrow 12. A restoring spring 13 is also illustrated, by way of which the movable element 11 is connected to the carrier device 9. A movable marker 4c (see FIG. 4B) is arranged at or on the movable element 11.

In this case, the markers 4a of the first marker group are arranged in a non-movable fashion relative to one another, in particular are secured to the carrier device 9. The movable marker 4c is movable relative to the markers 4a of the first marker group, in particular with the linear movement explained.

In a non-tensioned state of the restoring spring 13, the movable element 11 and thus also the movable marker 4c can be located in a first relative position (initial position) relative to the rigid markers 4a of the first marker group. With manual actuation of the movable element 11, for example with a user's thumb 10, the movable element 11 can be displaced from said first relative position, for example toward the markers 4a of the first marker group or away from the markers 4a of the first marker group. A relative position between the movable marker 4c and the markers 4a of the first marker group varies during this movement. If this position change is detected, a control signal SS can be generated.

In this case, the marker 4c illustrated in FIG. 4A is embodied as a so-called pushbutton marker. Specifically, if the user 10 releases the movable element 11, then this can return to the explained first relative position on account of the restoring spring 13. This advantageously enables simple handling for generating a control signal SS. The latter can be generated in particular if, after the deflection out of the initial position, the movable marker 4a has independently returned to the initial position again.

Figure 4C:
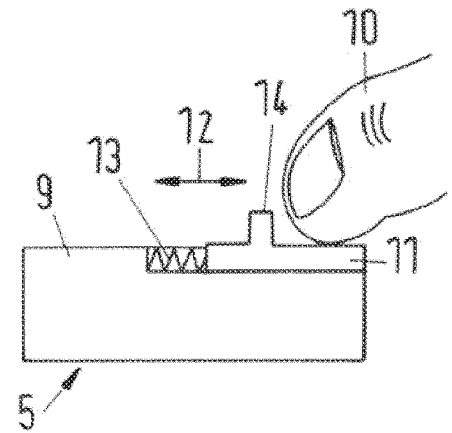
FIG. 4C shows a schematic side view of a marker array according to a further exemplary embodiment of the disclosure.
Figure 4B:
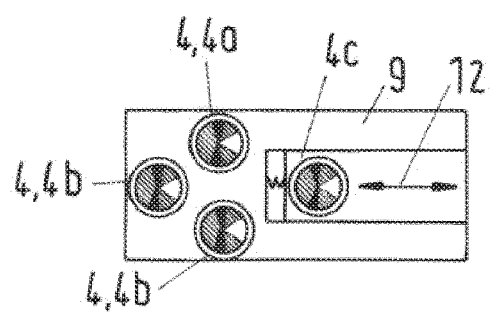
FIG. 4B shows a schematic plan view of the marker array illustrated in FIG. 4A.

FIG. 4C shows a schematic side view of a marker array 5 in accordance with a further exemplary embodiment of the disclosure. This exemplary embodiment illustrated in FIG. 4C is embodied substantially like the exemplary embodiment illustrated in FIG. 4A. Therefore, reference can be made to the corresponding explanations concerning FIG. 4A and FIG. 4B. In contrast to the exemplary embodiment illustrated in FIG. 4A, the movable element 11 includes an actuation section 14, which projects from the movable element 11 and can thus be actuated more simply and more reliably by a user, in particular by the user's thumb 10.

Figure 5A:
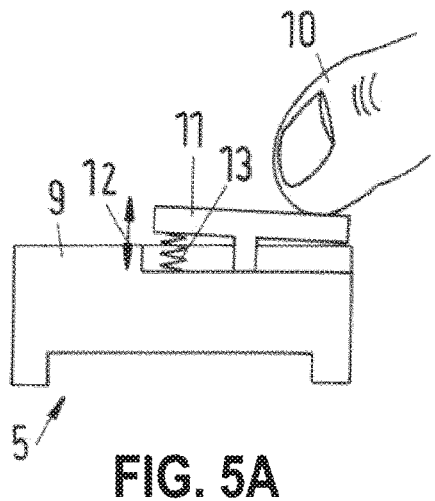
FIG. 5A shows a schematic side view of a marker array according to a further exemplary embodiment of the disclosure.

FIG. 5A shows a schematic side view of a marker array 5 in a further exemplary embodiment. The marker array 5 once again includes a carrier device 9 and also a movable element 10 mounted in a movable fashion on the carrier device 9. In this case, the movable element 11 is embodied as a tilting or rocking element. Markers 4a of a first marker group, which are non-movable relative to one another, are secured to the carrier device 9. A marker 4b (see FIG. 5B) arranged in a movable manner relative to said markers 4a is arranged on the movable element 11. A restoring spring 13 is furthermore illustrated. The movable element 11 can be tilted by actuation, for example with a user's thumb 10. A tilting movement in two directions is symbolized by an arrow 12. In this case, the tilting denotes a rotational movement about an axis that is not oriented parallel to a central axis or axis of symmetry of the movable element 11 or parallel to a central axis of the circular movable marker 4b, but rather in particular perpendicular thereto.

Figure 5B:
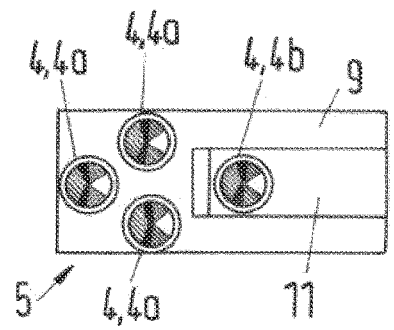
FIG. 5B shows a schematic plan view of the marker array illustrated in FIG. 5A.

FIG. 5B shows a schematic plan view of the marker array illustrated in FIG. 5A. The restoring spring is not tensioned in an initial position of the movable element 11. In said initial position, the movable marker 4b is located in a first relative position relative to the non-movable markers 4a. With actuation of the movable element 11, the marker 4b can be moved into a position different therefrom relative to the rigid markers 4a. If this position change is detected, then a control signal SS can be generated. If the actuation is canceled, for example if the movable element 11 is released, then the movable element 11 and also the marker 4b can return to the initial position on account of the restoring spring 13. Consequently, the exemplary embodiment illustrated in FIG. 5A and FIG. 5B advantageously enables the generation of a stateless control signal SS.

Figure 6A:
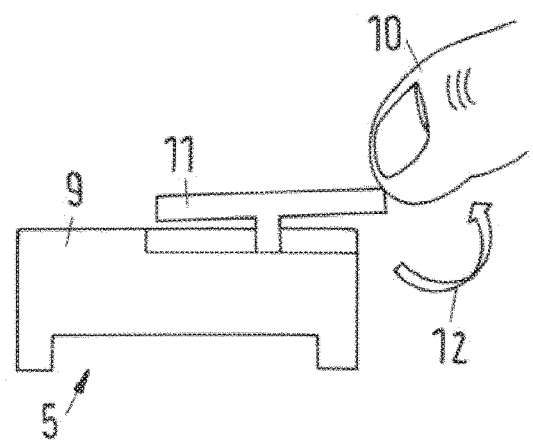
FIG. 6A shows a schematic side view of a marker array according to a further exemplary embodiment the disclosure.

FIG. 6A shows a schematic side view of a marker array 5 in a further exemplary embodiment. The marker array 5 includes a carrier device 9, wherein markers 4a of a first marker group, which are arranged in a non-movable fashion relative to one another, are once again arranged on the carrier device 9 (see, e.g., FIG. 6B). Furthermore, the marker array 5 includes a movable element 11, on which a movable marker 4b is arranged.

The movable element 11 is an element mounted in a rotatable fashion. In this case, the movable element 11 and thus also the movable marker 4b can carry out a rotational movement about a rotation axis.

It is possible for a central axis of symmetry or central axis of the circular movable marker 4b to be arranged concentrically with respect to the rotation axis. Alternatively, it is possible for the central axis of symmetry or central axis of the circular movable marker to be arranged indeed parallel but spaced apart by a predetermined distance from the central axis of rotation. This is illustrated, e.g., in FIG. 6B and FIG. 6C.

Figure 6B:
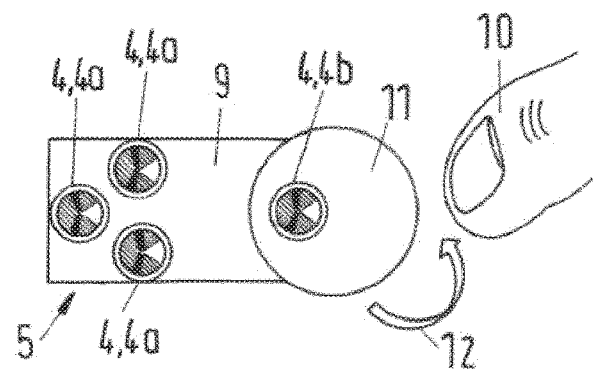
FIG. 6B shows a schematic plan view of the marker array illustrated in FIG. 6A in a first state.
Figure 6C:
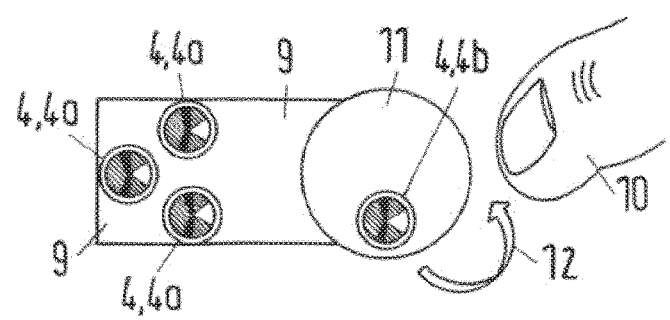
FIG. 6C shows a schematic plan view of the marker array illustrated in FIG. 6A in a second state.

FIG. 6B shows a schematic plan view of the marker array 5 illustrated in FIG. 6A in a first state. The non-movable markers 4a of the first marker group and the movable marker 4b arranged on the movable element 11 are evident. A rotational movement is symbolized by an arrow 12. In this case, FIG. 6B illustrates an initial position of the movable marker 4b. With rotation, the movable marker 4b can be moved into a second position different therefrom, which is illustrated in FIG. 6C. If this movement is detected, then a control signal SS can be generated. No restoring spring is illustrated in FIG. 6A, FIG. 6B, and FIG. 6C. It goes without saying, however, that it is conceivable for a restoring (rotary) spring to be arranged and/or embodied in such a way that the movable element can also be rotated by this restoring spring, in particular into the initial position again.

If no restoring spring is present, then the exemplary embodiment illustrated in FIG. 6A, FIG. 6B, and FIG. 6C can advantageously be used for generating a stateful control signal SS.

Moreover, mutually different control signals can be generated with the exemplary embodiment illustrated in FIG. 6A, FIG. 6B, and FIG. 6C. By way of example, mutually different control signals can be generated depending on the rotation angle of the rotation.

Figure 7A:
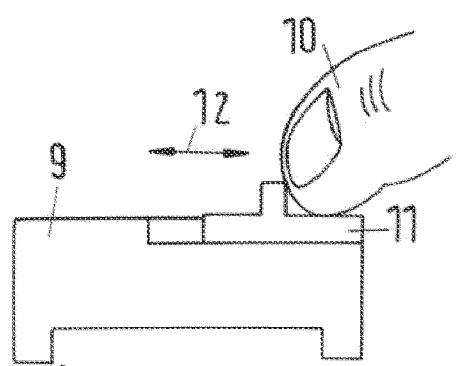
FIG. 7A shows a schematic side view of a marker array in in a first state according to a further exemplary embodiment the disclosure.
Figure 7B:
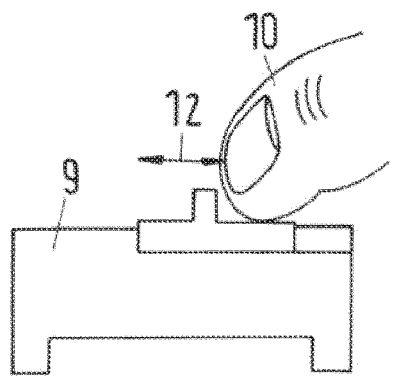
FIG. 7B shows a schematic side view of the marker array illustrated in FIG. 7A.
Figure 7C:
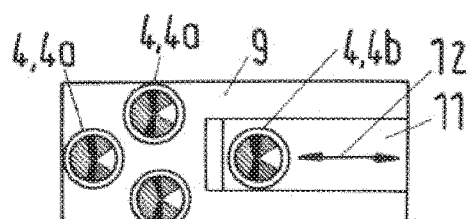
FIG. 7C shows a schematic plan view of the marker array illustrated in FIG. 7A.

FIG. 7A, FIG. 7B, and FIG. 7C show a marker array 5 in a further exemplary embodiment, wherein FIG. 7A illustrates a schematic side view in a first state of the marker array 5, FIG. 7B illustrates a schematic side view of the marker array 5 in a second state, and FIG. 7C illustrates a schematic plan view of the marker array 5. The marker array 5 illustrated in FIG. 7A, FIG. 7B, and FIG. 7C is embodied substantially like the marker array 5 illustrated in FIG. 4C. Therefore, reference can be made to the corresponding explanations concerning FIG. 4C. In contrast to the exemplary embodiment illustrated in FIG. 4C, the exemplary embodiment illustrated in FIG. 7A, FIG. 7B, and FIG. 7C does not include a restoring spring 13. FIG. 7A illustrates a first state of the marker array 5. FIG. 7C shows a schematic plan view of the marker array 5 in said first state. The illustration shows that the movable element 11 and thus the movable marker is located in a first relative position relative to the non-movable markers 4*a*. Said first relative position represents a first state. If the movable element 11 and thus also the movable marker 4*b* are put into said first state (with a linear movement) then a first control signal SS can be generated. FIG. 7B illustrates a schematic side view of the marker array 5 in a second state. The movable element 11 and thus also the movable marker 4*b* can be displaced with actuation, for example with a user's finger 10, with a linear movement toward the non-movable markers 4*a*. In this case, the relative position between the non-movable markers 4*a* and the movable marker 4*b* also changes. If it is detected that the relative position of the markers 4*a* and 4*b* with respect to one another has changed and the movable marker 4*b* is located in the second relative position following the change, it is possible, in particular, to generate a second control signal SS assigned to said second relative position.

From said second relative position, the movable marker can be put into the first state once again with actuation (see FIG. 7A). If it is detected that the relative position of the markers 4*a* and 4*b* with respect to one another has changed and the movable marker 4*b* is located in the first relative position following the change, it is possible, in particular, to generate a first control signal SS assigned to said first relative position. By way of example, the second control signal can be an activation signal for a specific operating mode of a controllable device. The first control signal can then be a deactivation signal for said operating mode.

Moreover, mutually different control signals can be generated with the exemplary embodiment illustrated in FIG. 7A, FIG. 7B, and FIG. 7C. By way of example, mutually different control signals can be generated depending on the path distance of the linear movement.

Figure 8A:
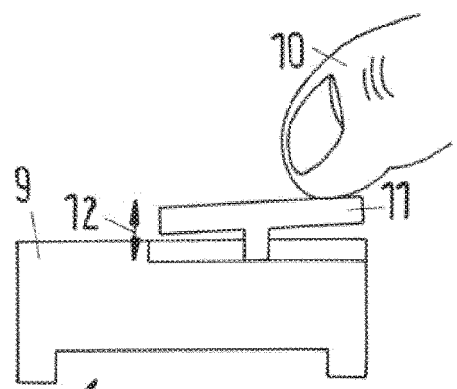
FIG. 8A shows a schematic side view of a marker array in a first state according to a further exemplary embodiment the disclosure.
Figure 8B:
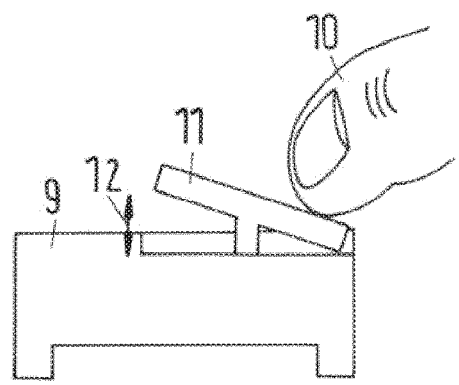
FIG. 8B shows a schematic plan view of the marker array illustrated in FIG. 8A.
Figure 8C:
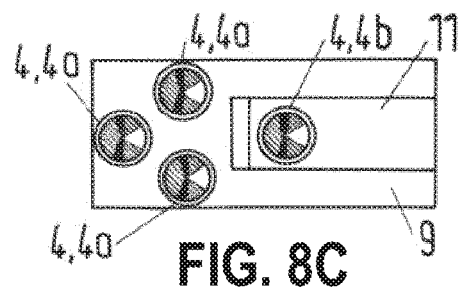
FIG. 8C shows a schematic side view of the marker array illustrated in FIG. 8A in a further state.

FIG. 8A, FIG. 8B, and FIG. 8C show a marker array 5 in a further exemplary embodiment, wherein FIG. 8A shows a schematic side view in a first state of the marker array 5, FIG. 8B shows a schematic side view of the marker array 5 in a second state, and FIG. 8C shows a schematic plan view of the marker array 5 illustrated in FIG. 8A, FIG. 8B, and FIG. 8C is embodied substantially like the marker array 5 shown in FIG. 5A. Therefore, reference can be made to the corresponding explanations concerning FIG. 5A. In contrast to the exemplary embodiment shown in FIG. 4C, the exemplary embodiment illustrated in FIG. 8A, FIG. 8B, and FIG. 8C does not include a restoring spring 13. FIG. 8A shows a first state of the marker array 5. FIG. 8C shows a schematic plan view of the marker array 5 in said first state. The illustration shows that the movable element 11 and thus the movable marker is located in a first relative position relative to the non-movable markers 4*a*. Said first relative position represents a first state. If the movable element 11 and thus also the movable marker 4*b* are put into said first state, that is to say tilted, then a first control signal SS can be generated. FIG. 8B shows a schematic side view of the marker array 5 in a second state. The movable element 11 and thus also the movable marker 4*b* can be moved with actuation, for example with a user's finger 10, with a tilting movement relative to the non-movable markers 4*a*. In this case, the relative position between the non-movable markers 4*a* and the movable marker 4*b* also changes. If it is detected that the relative position of the markers 4*a* and 4*b* with respect to one another has changed and the movable marker 4*b* is located in the second relative position following the change, it is possible, in particular, to generate a second control signal SS assigned to said second relative position.

From said second relative position, the movable marker can be put into the first state once again with actuation (see FIG. 8A). If it is detected that the relative position of the markers 4*a* and 4*b* with respect to one another has changed and the movable marker 4*b* is located in the first relative position following the change, it is possible, in particular, to generate a first control signal SS assigned to said first relative position.

By way of example, the second control signal can be an activation signal for a specific operating mode of a controllable device. The first control signal can then be a deactivation signal for said operating mode.

Figure 9:
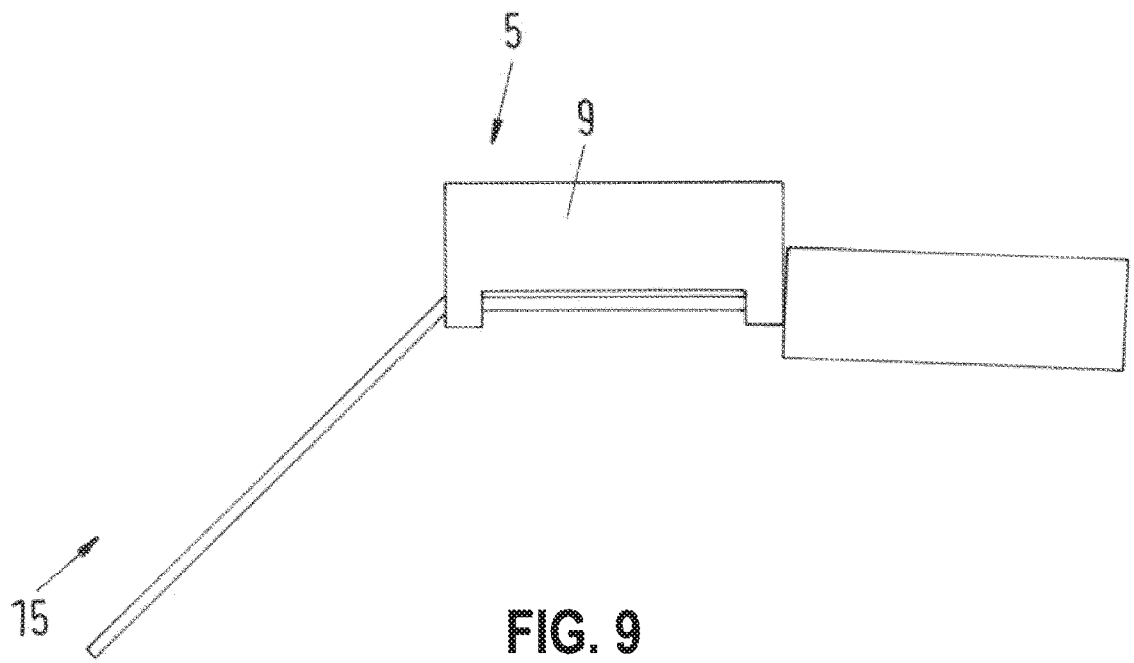
FIG. 9 shows a schematic side view of an instrument with a marker array according to an exemplary embodiment of the disclosure.

FIG. 9 shows a schematic side view of an instrument 15 with a marker array 5 according to an aspect of the disclosure. Only the carrier device 9 of the marker array 5 is illustrated. In this case, the marker array 5 can have securing means, e.g., clip or latching elements, in order to secure the marker array 5 to the instrument 15. The instrument 15 can be a suction device, for example.

In this case, it is possible that control signals SS for a controllable device 3, for example a surgical microscope that is movable in an actuator-assisted manner, can be generated with the suction device.

Figure 10:
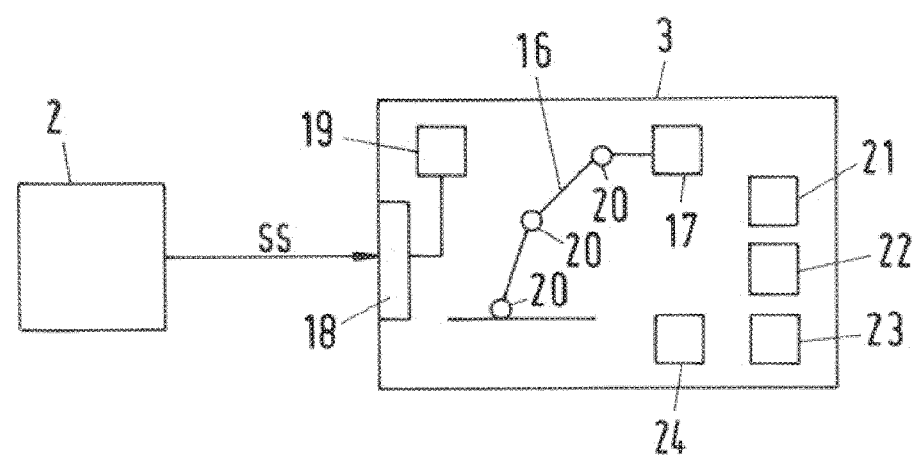
FIG. 10 shows a schematic block diagram of a controllable system including a system for generating a control signal according to a further exemplary embodiment of the disclosure.

FIG. 10 shows a schematic block diagram of a controllable system 1 in a further exemplary embodiment. The controllable system 1 includes a system 2 for generating a control signal SS, which can be embodied, e.g., as illustrated in FIG. 1. Furthermore, the controllable system 1 includes a controllable device 3 embodied as a positioning device 16. Said device can serve for positioning an object 17 to be positioned in space, wherein the object 17 to be positioned can be, e.g., a microscope or a measuring device of a coordinate measuring machine. The illustration shows that the positioning device 16 includes a plurality of drive devices 20 serving for moving movable parts of the positioning device 16.

An interface 18 of the controllable device 3 for receiving a control signal SS and also a control device 19 of the controllable device 3 are also illustrated. The control device 19 can control the controllable device 3 depending on the control signal SS. In particular, a control signal SS can be an activation signal or a deactivation signal for a specific operating mode of the controllable device 3. Alternatively or cumulatively, a control signal SS can serve for controlling operation of the controllable device 3 in the activated operating mode.

Moreover, it is possible for signals which, unlike the control signal SS, are not generated depending on the variation of the relative position between markers 4 to serve for controlling operation of the controllable device, in particular in an activated operating mode. As explained above, an operating mode can be, e.g., a position tracking mode. In this case, e.g., with the evaluation device 8 of the system 2 (see FIG. 1), a position change of the marker array 5 can be detected and a corresponding signal that codes said position change can be transmitted to the controllable device 3, e.g., via the interface 18 or a further interface (not illustrated). Then, in particular with the control device 19 of the controllable device 3, in an activated position tracking mode, the position of the object 17 to be positioned can be varied according to the position change of the marker array 5.

The illustration furthermore shows that the controllable device 3 can include an illumination device 21. In an activated illumination change mode or in an illumination intensity variation mode, it is possible to vary operation, in particular an illumination intensity, depending on the control signal SS or a signal different therefrom.

The illustration furthermore shows that the controllable device 3 can include an image capture device 22. In an activated camera zoom mode, a zoom value can be varied depending on the control signal SS or a signal different therefrom.

The illustration furthermore shows that the controllable device 3 can include a storage device 23. Depending on the control signal SS, a current spatial position of the object to be positioned can be stored in the storage device 23.

The illustration furthermore shows that the controllable device 3 can include a display device 24 for displaying input means. In an activated input mode, a user input can be effected depending on the control signal SS, e.g., by the generation of control signals SS, or a signal different therefrom, by a user.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS 1 controllable system
2 system for generating a control signal
3 controllable device
4 marker
4a non-movable markers
4b movable marker
5 marker array
6 optical position detection system
7 optical detection device
8 evaluation device
9 carrier device
10 thumb, finger
11 movable element
12 arrow
13 restoring spring
14 actuation section
15 instrument
16 positioning device
SS control signal

What is claimed is:

1. A method for generating a control signal for a controllable device with an optical position detection system, the method comprising:
generating images of at least one spatial region with at least one optical detection device of the optical position detection system;
identifying markers in the images;
generating the control signal when at least one of a relative position between at least two markers changes and a number of imaged markers changes,
wherein the controllable device is a positioning device,
wherein the control signal is an activation signal for activating a predetermined operating mode of the controllable device or a deactivation signal for deactivating the predetermined operating mode of the controllable device, and
wherein, in an activated operating mode, control signals which are different from the deactivation signal and which are generated depending on a change of at least one of the relative position between two markers and the number of imaged markers, serve for controlling an operation of the controllable device or parts of the controllable device.

2. The method as claimed in claim 1, further comprising: generating the control signal when the relative position changes in a predetermined manner.

3. The method as claimed in claim 1, further comprising: changing the relative position with a relative movement along a linear trajectory.

4. The method as claimed in claim 1, further comprising: changing the relative position by a relative movement along a trajectory in a shape of a circle arc or by a rotation of at least one marker.

5. The method as claimed in claim 1, further comprising: changing the relative position by a manual actuation of at least one marker.

6. The method as claimed in claim 1, further comprising: moving at least one marker out of an initial position; and generating, in a position that is different from the initial position, a restoring force/a restoring moment for moving the at least one marker into the initial position.

7. The method as claimed in claim 1, further comprising: moving at least one marker from an initial position into an end position without generating, in the end position, a restoring force/a restoring moment for moving the at least one marker into the initial position.

8. The method as claimed in claim 1, further comprising: interrupting or ending a marker-based position determination when the relative position between the at least two markers changes.

9. The method as claimed in claim 1, assigning mutually different control signals to at least one of mutually different changes and mutually different marker arrays subsequent to the change.

10. The method as claimed in claim 1, further comprising: identifying, depending on identified markers, a marker array comprising the at least two markers; and
generating the control signal depending on a relative position change between the at least two markers of the marker array.

11. The method as claimed in claim 1, wherein the predetermined operating mode is a position tracking mode.

12. The method as claimed in claim 1, wherein the predetermined operating mode is a measuring mode.

13. The method as claimed in claim 1, wherein the predetermined operating mode is an input mode.

14. A system for generating a control signal for activating a predetermined operating mode or deactivating the predetermined operating mode of a controllable positioning device with an optical position detection system, the system comprising:
at least one marker;
at least one optical detection device of the optical position detection system; and
at least one evaluation device,
wherein at least two images of at least one spatial region are generatable with the at least one optical detection device,
wherein markers are identifiable in the images with the at least one evaluation device,
wherein the control signal is generatable with the at least one evaluation device when at least one of a relative position between at least two markers changes and a number of imaged markers changes,
wherein the controllable positioning device is a positioning device, wherein the control signal is an activation signal for activating the predetermined operating mode of the controllable positioning device or a deactivation signal for deactivating the predetermined operating mode of the controllable positioning device, and wherein, in an activated operating mode, control signals which are different from the deactivation signal and which are generated depending on a change of at least one of the relative position between two markers and of the number of imaged markers, serve for controlling an operation of the controllable positioning device or parts of the controllable positioning device in an operating mode-specific manner.

15. A controllable system comprising:
at least one system for generating a control signal as claimed in claim 14; and
at least one controllable device.

16. The method as claimed in claim 1, wherein the controllable device is a positioning device for a microscope or a sensor of a coordinate measuring device.

* * * * *